United States Patent [19]

Tsaklakidis et al.

[11] Patent Number: 4,996,219

[45] Date of Patent: Feb. 26, 1991

[54] IMIDAZOLIDINE DERIVATIVES AS IMMUNOSUPPRESSIVES

[75] Inventors: Christos Tsaklakidis; Elmar Bosies, both of Weinheim; Michael Schultz, Mannheim; Rainer Haag, Ladenburg; Dieter Herrmann, Heidelberg; Wulf Pahlke, Bensheim, all of Fed. Rep. of Germany

[73] Assignee: Boehringer Mannheim GmbH, Mannheim, Fed. Rep. of Germany

[21] Appl. No.: 448,129

[22] Filed: Dec. 13, 1989

[30] Foreign Application Priority Data

Dec. 13, 1988 [DE] Fed. Rep. of Germany ....... 3841879

[51] Int. Cl.$^5$ ................... A61K 31/44; C07D 401/00; C07D 409/00; C07D 233/30
[52] U.S. Cl. ................................. 514/341; 548/309; 548/308; 546/278; 546/256; 514/333; 514/389
[58] Field of Search ............... 548/309, 308; 546/278, 546/256; 514/333, 341, 389

[56]  References Cited

U.S. PATENT DOCUMENTS 4,083,987  4/1978  Bicker et al. ........................ 548/309

Primary Examiner—Mary C. Lee
Assistant Examiner—Robert C. Whittenbaugh
Attorney, Agent, or Firm—Armstrong, Nikaido, Marmelstein, Kubovcik & Murray

[57] ABSTRACT

The present invention provides compounds of the general formulae:

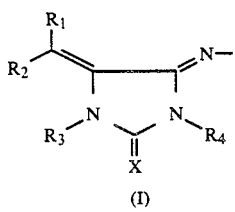 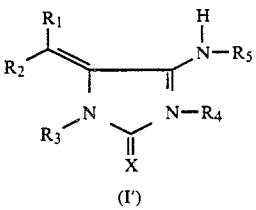

(I)  (I')

wherein $R_1$ and $R_2$, which can be the same or different, are hydrogen atoms or $C_1$-$C_5$-alkyl radicals, $C_3$-$C_5$-alkenyl radicals or phenyl radicals or, together with the carbon atom to which they are attached, form a saturated or unsaturated $C_3$-$C_7$ ring, $R_3$ and $R_4$, which can be the same or different, are hydrogen atoms, straight-chained or branched $C_1$-$C_{10}$-alkyl radicals, straight-chained or branched $C_3$-$C_7$-alkenyl radicals, $C_3$-$C_7$-cycloalkyl radicals, $C_3$-$C_7$-cycloalkenyl radicals, phenyl, arylalkyl or hetarylalkyl radicals, $R_5$ is a hydrogen atom or a lower alkyl radical and X is an oxygen or sulphur atom or an imino group.

The present invention also provides processes for the preparation of these compounds, as well as pharmaceutical compositions with immunosuppressive action containing them.

33 Claims, No Drawings

IMIDAZOLIDINE DERIVATIVES AS IMMUNOSUPPRESSIVES

The present invention is concerned with new imidazolidine derivatives and processes for their preparation, as well as with medicaments which contain these compounds.

In general, immunosuppressives as such have already been known for a comparatively long time (Pharmazie unserer Zeit, 1, 2-8/1972 and 12, 20-29/1983). The expression "immune suppression" used in this connection thereby designates, in general, the non-specific suppression of the immune response, for example with the help of antisera, ionising radiations or special therapeutics.

These chemotherapeutics are used after the transplantation of tissues or organs and in the therapy of autoimmune diseases. They inhibit the proliferation of lymphocytes by direct intervention into the DNA and RNA synthesis. This class of compounds includes cyclosporins, folic acid antagonists, purine analogues, alkylating substances, such as cyclophosphamide and certain corticosteroids. However, the disadvantage of these previously used immunosuppressives is the increased extent of susceptibility to infection to be observed in the treated organism since the whole of the body's immune system is weakened and not only the humoral but also the cellular immune response are suppressed.

The immune-suppressive properties of the immunosuppressives at present known, for example cytostatics and corticosteroids, are dosage-dependent but nonselective, i.e. they act on all immune-competent cells. These compounds inhibit not only the humoral but also cellular immune response to a number of antigens and act non-specifically on T and B lymphocytes.

Therefore, there is a very great interest for immunosuppressives which interfere specifically with pathologically strengthened or increased immune mechanisms without, however, influencing the natural immune reactions normally taking place in the body. Such specifically effective immuno-suppressive substances are hitherto not known.

Therefore, it is an object of the present invention to provide such new immunosuppressively-effective agents.

Surprisingly, we have now found that the compounds according to the present invention achieve this object and can be used as advantageous immunosuppressives. They specifically suppress the B cell proliferation or B cell activation. They can be used advantageously for the treatment of all diseases in which a polyclonal activation or proliferation of B cells is of pathophysiological, sympathomatic or clinical relevance.

In this sense, there can be mentioned the treatment of the following diseases: autoimmune diseases, such as rheumatoid arthritis, diabetes mellitus type I, psoriasis, lupus systemicus erythematosus; rejection reactions after tissue or organ transplantations, for example of skin, bone marrow and kidneys, viral and retroviral infections of every genesis, for example ARC (AIDS-related complex) and AIDS, as well as its preliminary stages; as well as B cell leukaemias and lymphomas, for example chronic lymphatic leukaemia, lymphoblastic lymphoma (such as Burkitt's lymphoma and the like) and B cell/plasma cell neoplasias, for example plasmacytoma (multiple myeloma) and the like. In the literature, autoimmune diseases are designated as being those diseases which are involved with the formation of autoantibodies. These autoantibodies are directed against the body's own antigens and thus bring about a defence against the body's own substances. It is desirable to suppress this pathological over-reaction of the immune system with specifically active immunosuppressives.

In the meaning of the present invention, the expression "immunosuppression" is to be understood to include, in general, all aspects of the naturally induced immunological non-response, the artificially induced non-response and the pathologically induced tolerance of an individual to auto- and foreign antigens.

Thus, according to the present invention, there are provided new imidazolidine derivatives of the general formula:

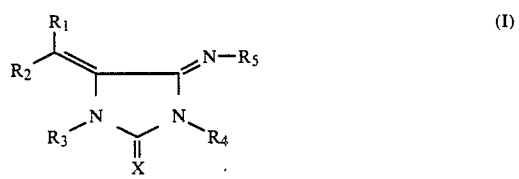

wherein $R_1$ and $R_2$, which can be the same or different, are hydrogen atoms or $C_1$–$C_5$-alkyl radicals, $C_3$–$C_5$-alkenyl radicals or phenyl radical or, together with the carbon atom to which they are attached, form a saturated or unsaturated $C_3$–$C_7$ ring, $R_3$ and $R_4$, which can be the some or different, are hydrogen atoms, straight-chained or branched $C_1$–$C_{10}$-alkyl radicals, straight-chained or branched $C_3$–$C_7$-alkenyl radicals, $C_3$–$C_7$-cycloalkyl radicals, $C_3$–$C_7$-cycloalkenyl radicals, phenyl, arylalkyl or hetarylalkyl radicals, $R_5$ is a hydrogen atom or a lower alkyl radical and X is an oxygen or sulphur atom or an imino group (=NH).

When $R_4$ is a hydrogen atom, the compounds of general formula I can also be present in the isomeric form I':

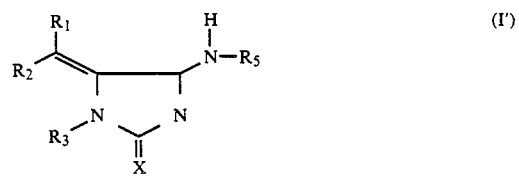

in which $R_1$, $R_2$, $R_3$ and $R_5$ have the same meanings as in general formula I.

The $C_1$–$C_5$-alkyl radical $R_1$ and $R_2$ is a methyl, ethyl, n-propyl, isopropyl, butyl, isobutyl, pentyl or isopentyl radical and especially a methyl radical; the $C_3$–$C_5$-alkenyl radical is an allyl, butenyl, isobutenyl, pentenyl or isopentenyl radical and especially an allyl radical; and the $C_3$–$C_7$ ring is preferably a cyclopropyl, cyclopentyl or cyclohexyl radical.

The $C_1$–$C_{10}$-alkyl radical $R_3$ and $R_4$ is preferably a methyl, ethyl, propyl, isopropyl, butyl, isobutyl, n-pentyl, isopentyl, neopentyl, n-hexyl, isohexyl, n-octyl or n-decyl radical and especially a methyl, propyl, isopropyl, neopentyl or n-hexyl radical; the $C_3$–$C_7$-alkenyl radical of $R_3$ and $R_4$ is preferably an allyl, butenyl, isobutenyl, pentenyl, hexenyl or heptenyl radical and especially an allyl or isobutenyl radical; the $C_3$–$C_7$-cycloalkyl radical is preferably a cyclopropyl, cyclohexyl or cycloheptyl radical and especially a cyclopropyl or cyclohexyl radical; the $C_3$-$C_7$-cycloalkenyl radical is preferably a cyclopentenyl or cyclohexenyl radical; the arylalkyl substituent $R_3$ and $R_4$ is preferably a benzyl radical; and the hetarylalkyl radical is preferably a picolyl, thienyl or furfuryl radical.

The lower alkyl radical $R_5$ is preferably a methyl, ethyl or propyl radical.

The compounds of general formula I according to the present invention can be prepared, for example, as follows:

(a) when $R_5$ is a hydrogen atom, a compound of the general formula:

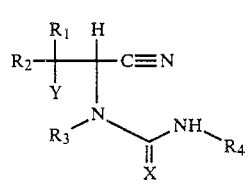  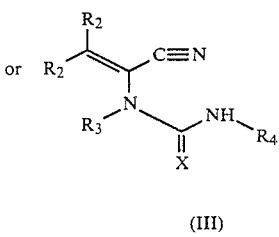

(II)          (III)

in which $R_1$, $R_2$, $R_3$, $R_4$ and X have the above-given meanings and Y in general formula II is a group which can be removed, such as a halogen atom or a sulphonic acid ester or acyloxy radical, is reacted with a base, or (b) when X in the compound of general formula I is a sulphur atom or an imino group, the carbonyl group of a compound of the general formula:

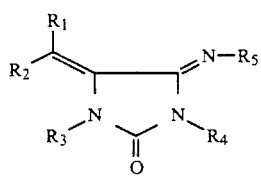

(IV)

in which $R_1$, $R_2$, $R_3$, $R_4$ and $R_5$ have the above-given meanings, is converted in known manner into a thiocarbonyl or imino group, or (c) when, in the compound of general formula I, X is an oxygen atom and $R_3$ and $R_4$ have the above-given meanings but are not simultaneously hydrogen atoms or the phenyl radicals, a compound of the general formula:

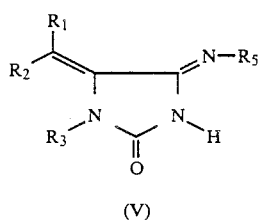  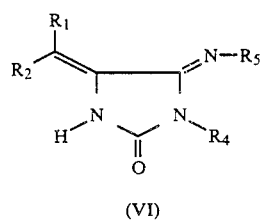

(V)          (VI)

in which $R_1$, $R_2$, $R_3$, $R_4$ and $R_5$ have the above-given meanings, is reacted in known manner with a compound of the general formula:

Y—$R_6$          (VII)

in which Y has the above-given meaning and $R_6$ has the same meaning as $R_3$ or $R_4$, with the exception of the meanings hydrogen and phenyl, or (d) a compound of the general formula:

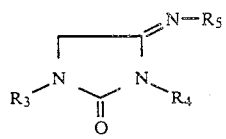

(VIII)

in which $R_3$, $R_4$ and $R_5$ have the above-given meanings, is reacted with a compound of the general formula:

(IX)

in which $R_1$ and $R_2$ have the above-given meanings, with the help of a condensation agent, or (e) when X in general formula I is an oxygen atom, a compound of the general formula:

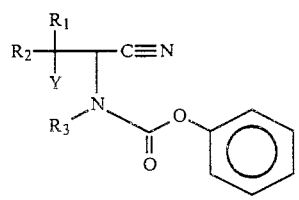

(X)

in which $R_1$, $R_2$, $R_3$ and Y have the above-given meanings, is reacted with a primary amine of the general formula:

$R_4$—$NH_2$          (XI)

in which $R_4$ has the above-given meaning, or (f) possibly subsequently converts a compound of general formula I, in which $R_5$ is a hydrogen atom, by alkylation into a compound of general formula I in which $R_5$ is a lower alkyl radical, or (g) when $R_1$, $R_2$, $R_3$, $R_4$ and $R_5$ in general formula I are hydrogen atoms, the compound 4-imino-1,3-diazabicyclo[3.1.0]hexan-2-one is subjected to a hydrolysis, or (h) when $R_4$ and $R_5$ are hydrogen atoms and X is an oxygen atom, a compound of the general formula:

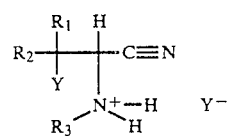

(XII)

in which $R_1$, $R_2$, $R_3$ and Y have the above-given meanings, is reacted with chlorosulphonyl isocyanate.

The compound 4-imino-1,3-diazabicyclo[3.1.0]hexan-2-one can be prepared according to the process described in Federal Republic of Germany Patent Specification No. 25 30 398. (U.S. Pat. No. 4,083,978).

As bases for the cyclisation of compounds of general formulae II and III to give compounds of general formula I according to the present invention, as a rule, there can be used aqueous solutions of alkali metal hydroxides, for example aqueous sodium or potassium hydroxide solution or the like alcoholic sodium or potassium hydroxide solution, an alcoholate, for example sodium or potassium methylate, sodium or potassium ethylate or potassium tert.-butylate, or a nitrogen base, for example triethylamine, 1,5-diazabicyclo[4.4.0]non-5-ene (DBN) or 1,8-diazabicyclo[5.4.0]undec-7-ene (DBU). As a rule, the reaction is carried out in water, an alcohol or an inert solvent, for example diethyl ether, tetrahydrofuran or toluene, and at a temperature of from −10° C. to 60° C. and preferably at ambient temperature. If a compound of general formula II is reacted to give a compound of general formula I according to the present invention, then at least 1.2 mole equivalents of base are required, whereas the cyclisation of compounds of general formula III to give compounds of general formula I is carried out with a catalytic amount of the base used.

Compounds of general formula II or X can be prepared by reacting a compound of general formula XII with a compound of the general formula:

$$R_4-N=C=X \qquad (XIII)$$

in which $R_4$ and $X$ have the above-given meanings, or with phenyl chlorocarbonate in water or in an inert solvent, for example toluene, diethyl ether or methylene chloride, or in a two-phase system, such as water/methylene chloride, with the use of a base, for example sodium hydroxide, potassium hydroxide, sodium bicarbonate, sodium carbonate or triethylamine, and at a temperature of from −10° C. to 60° C. and preferably at ambient temperature.

Compounds of general formula III are obtained either from compounds of general formula II by splitting off H—Y from the latter by means of an elimination agent or by reacting a compound of general formula X with an amine of general formula IX. As elimination agents, there can be used, for example, tertiary nitrogen bases, such as triethylamine, DBN or DBU.

The conversion of the carbonyl group of a compound of general formula IV into a thiocarbonyl or imino group is carried out by methods known from the literature, for example, by the reaction of a compound of general formula IV with phosphorus persulphide ($P_4S_{10}$) (Liebigs Ann. Chem., 746, 92/1971) or with Lawesson's reagent (Bull. Soc. Chim. Belg., 87, 223, 229, 525/1978) or with phenyl phosphorodiamidate (J. Heterocycl. Chem. 9, 1235/1972).

Compounds of general formula XII can be prepared by reacting a cyanoaziridine of the general formula:

(XIV)

in which $R_1$, $R_2$ and $R_3$ have the above-given meanings, with two equivalents of an acid of the general formula:

$$H-Y \qquad (XV)$$

in which Y has the above-given meaning.

Compounds of general formula XIV can be prepared by the process described in Federal Republic of Germany patent specification Ser. No. 28 33 986.(U.S. Pat. No. 4,321,194)

The reaction of a compound of general formula X with a compound of general formula XI takes place in water, alcohol or in an inert solvent, for example toluene, methylene chloride or diethyl ether, and at a temperature of from −10° C. to 60° C.

The reaction of a compound of general formula VIII with a compound of general formula IX is carried out in water, alcohol or an inert solvent, for example toluene or diethyl ether, with the addition of a condensation agent. As condensation agent, there is usually employed an alkali metal hydroxide, for example potassium hydroxide, an alkali metal alcoholate, for example sodium ethylate or potassium tert.-butylate, or a nitrogen base, for example morpholine or piperidine (Biochem. J., 29, 2256/1935).

Compounds of general formula VIII can be prepared by methods known from the literature (see e.g. A.F.A. Shalaby, H.A. Daboun, Z. Naturforsch., 306, 124/1975).

The reaction of compounds of general formula XII with chlorosulphonyl isocyanate takes place by methods known from the literature (A.V. Narender Reddy, Synth. Commun., 18(5), 525/1988).

For the preparation of pharmaceutical compositions, the compounds according to the present invention are mixed in known manner with appropriate pharmaceutical carrier substances, possibly granulated and pressed, for example into tablets or dragee cores. Filling the mixture into hard capsules is also possible. With the addition of appropriate adjuvant materials, there can also be produced a solution or suspension in water, an oil, such as olive oil, or a high molecular weight polymer, such as polyethylene glycol, and administered as injection solutions, soft gelatine capsules, syrups or drops.

As solid carrier materials, there can be used, for example, starch or starch derivatives, sugars, sugar alcohols, celluloses or cellulose derivatives, tensides, talc, highly dispersed silicic acids, high molecular weight fatty acids or the salts thereof, gelatine, agar-agar, calcium phosphate, animal or vegetable fats or waxes or solid high molecular weight polymers, such as polyethylene glycols or polyvinylpyrrolidones. Compositions suitable for oral administration can, if desired, contain flavouring and sweetening materials.

An especially preferred pharmaceutical composition is a film tablet containing 100 mg. of active material which has the following composition:

|  | weight/piece/mg. |
|---|---|
| active material | 100.000 |
| lactose monohydrate | 63.000 |
| poly-(0-carboxymethyl)-starch, sodium salt | 7.000 |
| poly-(1-vinyl-2-pyrrolidone) 25,000 | 4.000 |
| poly-(0-carboxymethylstarch, sodium salt | 3.000 |
| microcrystalline cellulose | 20.000 |
| silicon dioxide, highly dispersed | 1.500 |
| magnesium stearate | 1.500 |
| core weight: | 200.000 |

The film tablets are then produced by film drageeing the active material cores obtained in the usual way.

Film tablets with, for example, 10 mg., 50 mg., 200 mg. or 500 mg. of active material are produced in a corresponding manner.

The dosaging of the active material depends upon the age and sex of the individual, as well as upon the nature of the indication to be treated.

In principle, 0.1 to 100 mg. per kg. of body weight can be administered daily orally, intravenously, subcutaneously or intramuscularly. However, amounts of 5 to 50 mg./kg. body weight and especially 5 to 20 mg./kg. body weight are preferred. The amounts of active material can be administered 1 to 3 times daily.

Besides the compounds described in the following Examples, the following compounds are also especially preferred according to the present invention:

(BV1) 4-imino-5-methyleneimidazolidine-2-thione
(BV2) 2,4-diimino-5-methyleneimidazolidine
(BV3) 4-imino-5-n-hexylideneimidazolidin-2-one
(BV4) 1-methyl-4-imino-5-methyleneimidazolidin-2-one
(BV5) 1-isopropyl-4-imino-5-methyleneimidazolidin-2-one
(BV6) 1-n-hexyl-4-imino-5-methyleneimidazolidin-2-one
(BV7) 1-allyl-4-imino-5-methyleneimidazolidin-2-one
(BV8) }-cyclopropyl-4-imino-5-methyleneimidazolidin-2-one
(BV9) 1-(3-pyridylmethyl)-4-imino-5-methylenelmldazolidin2-one
(BV10) 1-phenyl-4-imino-5-methyleneimidazolidin-2-one
(BV11) 3-methyl-4-imino-5-methyleneimidazolidin-2-one, m.p. Z30° C. (decomp.)
(BV12) 3-n-propyl-4-imino-5-methyleneimidazolidin-2-one, m.p. 130° C. (decomp.)
(BV13) 3-(2 2-dimethylpropyl)-4-imino-5-methyleneimidazol idin-2-one
(BV14) 3-cyclohexyl-4-imino-5-methyleneimidazolidin-2-one, m.p.,163°-164° C.
(BV15) 3-isobutenyl-4-imino-5-methyleneimidazolidin-2-one
(BV16) 3-(4-pyridylmethyl)-4-imino-5-methyleneimidazolidin2-one, m.p. 194°-196° C.
(BV17) 3-phenyl-4-imino-5-methyleneimidazolidin-2-one. m.p. 208°-210° C.
(BV18) 1,3-dimethyl-4-imino-5-methyleneimidazolidin-2-one
(BV19) 4-imino-5-cyclohexylideneimidazolidin-2-one
(BV20) 4-imino-5-benzylideneimidazolidin-2-one
(BV21) 1,3-dimethyl-4-methyliminoimidazolidin-2-one
(BV22) 1,3-di-n-propyl-4-propyliminoimidazolidin-2-one.

The following Examples are given for the purpose of illustrating the present invention:

EXAMPLE 1 4-Imino-5-methyleneimidazolidin-2-one

To the solution of 2.79 g. (19.8 mmol) 2-amino-3-chloropropionitrile hydrochloride (m.p. 160° C.) in 20 ml. 2N sodium carbonate solution is simultaneously added dropwise at ambient temperature and with good stirring a solution of 3.2 g. (20 mmol) phenyl chloroformate in 20 ml. diethyl ether and 20 ml. 2 N sodium carbonate solution. Thereafter, the reaction mixture is stirred for 2 hours at ambient temperature, the ethereal phase is separated Off, washed once with water and dried over anhydrous sodium sulphate. After stripping off the solvent under reduced pressure, the residue is recrystallised from toluene to give 3.82 g. (85% of theory) 2-(phenoxycarbonylamino)-3-chloropropionitrile; m.p. 103–105° C.

A suspension of 3.25 g. (14.5 mmol) 2-(phenoxycarbonylamino)-3-chloropropionitrile in 30 ml. 2 N aqueous ammonia solution is stirred for 1 hour at ambient temperature, the precipitate obtained is filtered off with suction and washed with a little cold water and diethyl ether to give 1.24 g. (66% of theory) of the title compound which contains 1 mole water of crystallisation; m.p. >300° C.

EXAMPLE 2

Starting from 2-amino-3-chlorobutyronitrile hydrochloride (m.p. 181° C.), 4-imino-5-ethylideneimidazolidin2-one is prepared analogously; yield: 69% of theory; m.p. 252° C.

EXAMPLE 3

4-Imino-5-isopropylideneimidazolidin-2-one

A solution of 6 g. (62.5 mmol) 2-cyano-3,3-dimethylaziridine in 30 ml. 6N hydrochloric acid is stirred for 45 minutes at 50° C. Subsequently, the solution is evaporated to dryness and the residue is recrystallised from isopropanol to give 2.2 g. (21% of theory) 2-amino-3-chloro-3-methylbutyronitrile hydrochloride; m.p. 182°–184° C.

To a solution of 2.2 g. (13 mmol) 2-amino-3-chloro-3-methylbutyronitrile hydrochloride in 15 ml. 2N sodium carbonate solution is simultaneously added dropwise at ambient temperature and with good stirring a solution of 2.24 g. (14.3 mmol) phenyl chloroformate in 15 ml. diethyl ether and 15 ml. 2N sodium carbonate solution. Thereafter, the reaction mixture is stirred for 2 hours at ambient temperature, the ether phase is separated off, washed once with water and dried over anhydrous sodium sulphate. After stripping off the solvent under reduced pressure, the residue is recrystallised from toluene to give 3.2 g. (98% of theory) 2-(N-phenoxycarbonylamino)-3-chloro-3-methylbutyronitrile; m.p. 98°–100° C.

A suspension of 2 g. (7.9 mmol) 2-(N-phenoxycarbonylamino)-3-chloro-3-methylbutyronitrile in 20 ml. 2N ammonia is stirred for 4 hours at ambient temperature. The precipitate is then filtered off with suction and washed with a little cold water and diethyl ether to give 0.7 g. (64% of theory) 2-(N-aminocarbonylamino)-3-methylcrotonic acid nitrile; m.p. 204°–206° C.

To a suspension of 0.42 g. (3 mmol) 2-(N-aminocarbonylamino)-3-methylcrotonic acid nitrile in 6 ml. absolute ethanol is added dropwise, while stirring, within 5 minutes, a solution of 10 mg. sodium in 2 ml. absolute ethanol. Subsequently, the reaction mixture is further stirred for 2.5 hours at ambient temperature and the precipitate is then filtered off with suction and washed with ethanol and diethyl ether to give 0.32 g. (76.6% of theory) of the title compound; m.p. 258° C. (decomposition).

EXAMPLE 4

3-Benzyl-4-imino-5-methyleneimidazolidin-2-one

A solution of 1.35 ml. (11 mmol) benzyl isocyanate in 10 ml. methylene chloride is added dropwise, with vigorous stirring at ambient temperature, to a solution of 1.41 g. (10 mmol) 2-amino-3-chloropropionitrile hydrochloride in 11 ml. 1N aqueous sodium carbonate solution. Subsequently, the reaction mixture is stirred for 2 hours at ambient temperature and the organic phase is then separated off, washed with water and dried over anhydrous sodium sulphate. After stripping off the solvent, the residue is recrystallised from diethyl ether to give 1.75 g. (73.8% of theory) 2-(benzylaminocarbonylamino)-3-chloropropionitrile; m.p. 110°–112'

A solution of 4.75 g. (20 mmol) 2-(benzylaminocarbonylamino)-3-chloropropionitrile and 6 ml. triethylamine in 50 ml. dry tetrahydrofuran is heated to reflux for 5 hours. Subsequently, the precipitate formed is filtered off, the filtrate is evaporated to dryness and the residue is chromatographed on silica gel (elution agent: ethyl acetate) to give 2.5 g. (62.2% of theory) of the title compound; m.p. 139°–141° C.

EXAMPLE 5

1-Benzyl-4-imino-5-methyleneimidazolidin-2-one

A solution of 6 g. (37.8 mmol) 1-benzyl-2-cyanoaziridine in 30 ml. 6N hydrochloric acid is stirred for 1 hour at ambient temperature. Subsequently, the precipitate formed is filtered off with suction and successively washed with a little cold water, isopropanol and diethyl ether and dried in a desiccator to give 5.4 g. (62% of theory) of 2-benzylamino-3-chloropropionitrile hydrochloride; m.p. 161°–162° C.

To an ice-cooled solution of 4 g. (17.3 mmol) 2-benzylamino-3-chloropropionitrile in 40 ml. dry methylene chloride and 2.4 ml. triethylamine is added dropwise a solution of 1.64 ml. (18.9 mmol) chlorosulphonyl isocyanate in 20 ml. dry methylene chloride. Subsequently, the reaction solution is further stirred for 2 hours at 0° C., then warmed to ambient temperature and mixed with 300 ml. of a 5% aqueous solution of sodium hydrogen carbonate. The organic phase is then separated off, dried over anhydrous sodium sulphate and evaporated to dryness. Subsequently, the residue is chromatographed on silica gel (elution age t: merhaol/methylene chloride 1:10 v/v) to give 0.8 g. (24% of theory) of the title compound; m.p. 225° C.

TEST REPORT

In vitro tests

Methodology (a) Concanavalin-A induced lymphocyte proliferation (LPT)

Mice splenocytes are adjusted in RPMI 1640 medium (with conventional additions of streptomycin, penicillin, L-glutamine and 10% fetal calf serum) to a cell density of $2 \times 10^6$ viable cells per ml. 200 µl of this cell suspension are mixed with 20 µl of an 11-fold concentrated solution of the substance to be tested. 0,5 /µg of Concanavalin A in 10 µl of phosphate buffered saline solution (PBS) are added as mitogenic stimulus to each culture. 5 hours before the end of the 48 h incubation period, the individual cultures receive 20 /µl of a 3H-thymidine solution and the proliferation of the cells is determined by means of incorporated radioactivity.

(b) Tumor-growth Inhibition Test

A Meth A fibrosaccoma cell line is passaged weekly as ascites in mice. After the ascites is punctured, the cells are washed and adjusted to a cell density of $5 \times 10^4$ vital cells/ml in the aforementioned medium. 200 /µl of this suspension are pipetted into the cavities of a microtitration plate and solution of the substances to be tested are added as above. 3 hours before the end of the 48 h incubation period 3H thymidine is added. The proliferation of the individual cultures is determined by the incorporated radioactive thymidine.

(c) Interleukin-2 dependent proliferation of human T-lymphocytes (IL-2)

The mononuclear cell fraction is separated from heparinized human whole blood by means of a Ficoll gradient. After washing twice, the cell number is adjusted to $1 \times 10^6$ ml and incubation is carried out with 3 /µg/ml of Concanavalin A for 3 days. After washing twice, the cell number is set to $5 \times 10^5$ cells/ml. 160 /µl of this cell suspension are incubated with 20 /µl IL-2 and 20 /µl of a dilution of the test substance in microtitration plates for a total of 48 h. 4 hours before the end of incubation, 3H thymidine is added. The proliferation of the cultures is determined by means of the incorporated radioactivity.

(d) B-cell growth factor dependent proliferation of human B lymphocytes (BCGF).

The macrophage/monocytes are removed from the mononuclear cell fraction (see above) by adhesion to plastic petri dishes. T lymphocytes are separated by rosetting with neuraminidase-treated sheep erythrocytes. The enriched human B-lymphocyte population so obtained is adjusted to $3 \times 10^5$/ml. 160 /µl of this suspension together with 10 /µl of BCGF (B cell growth factor) and 20 /µl of the substance dilution to be tested are incubated for a total of 140 h. 16 h before the end of incubation, 3H thymidine is added and analysis is carried out as already described.

Test results

The attached table shows the IC$_{50}$ values which were determined graphically from a plot of the mean of sixfold measured inhibition values versus the concentrations tested in rows differing by factor ⅓ on probability paper. For the upper two compounds the means plus standard deviations from n experiments are shown.

IMEXON = 4-imino-1,3-diazabicyclo[3.1.0]hexan-2-one (compound of U.S. Pat. No. 4,083,987)

TABLE

| Compound | Test No. | IC$_{50}$ (/µg/ml) | | | |
|---|---|---|---|---|---|
| | | LPT | TGI | IL 2 | BCGF |
| Imexon | | 6,3 ± 1,5 (n = 6) | 11,3 ± 4,4 (n = 5) | 5,1 ± 2,1 (n = 5) | 0,9 ± 0,3 (n = 4) |
| Ex. 1 | | 3,9 ± 0.7 (n = 4) | >10,3 ± 4,1 (n = 4) | 2,6 ± 0,7 (n = 2) | 1,9 ± 1,5 (n = 3) |
| Ex. 2 | 1 | 12,0 | 22,6 | >10 | ~4,7 |
| | 2 | 11,1 | >30 | >10 | 10,6 |
| Ex. 3 | 1 | 20,7 | >30 | >30 | >3 |
| | 2 | >10 | >10 | >10 | >10 |
| Ex. 4 | 1 | <3 | 2,8 | <3 | <3 |
| | 2 | 0,69 | 1,8 | 1,2 | 1,6 |
| | 3 | 0,52 | 3,1 | 2,0 | 1,6 |
| Ex. BV11 | 1 | <3 | 4,2 | ≦3 | <3 |
| | 2 | 0,92 | 2,3 | 3,5 | 0,71 |
| Ex. BV12 | 1 | <3 | 7,5 | 5,1 | 3,2 |
| | 2 | 1,2 | 3,9 | 4,6 | 2,6 |
| | 3 | 1,1 | 4,9 | | |
| Ex. BV14 | 1 | <3 | 3,8 | <3 | <3 |
| | 2 | 1,0 | 2,7 | 1,3 | 1,6 |
| | 3 | 1,4 | 5,5 | 3,6 | 1,5 |
| Ex. BV16 | 1 | <3 | 3,9 | 3,5 | <3 |
| | 2 | 0,80 | 5,1 | 4,8 | 0,74 |
| | 3 | 0,90 | 5,5 | | 1,1 |
| Ex. BV17 | 1 | <3 | <3 | <10 | <3 |
| | 2 | 0,82 | 2,1 | 1,4 | 0,90 |
| | 3 | 0,64 | 3,5 | 2,4 | 1,7 |

We claim:

1. A compound of the formula

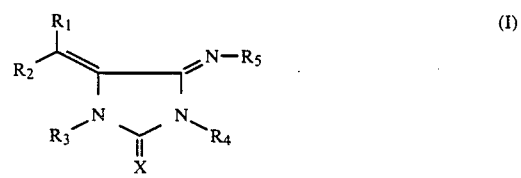

(I)

wherein
- $R_1$ and $R_2$, which can be the same or different, are a hydrogen atom, a $C_1$-$C_5$ alkyl radical, a $C_3$-$C_5$ alkenyl radical, a phenyl radical, or $R_1$ and $R_2$, together with the carbon atom to which they are attached, form a saturated or unsaturated hydrocarbon $C_3$-$C_7$ ring;
- $R_3$ and $R_4$, which can be the same or different, are a hydrogen atom, a straight chained or branched $C_1$-$C_{10}$ alkyl radical, a straight-chained or branched $C_3$-$C_7$ alkenyl radical, a $C_3$-$C_7$ cycloalkyl radical, a $C_3$-$C_7$ cycloalkenyl radical, phenyl radical, a $C_6$-$C_{10}$-aryl-$C_1$-$C_6$-alkyl radical, or a hetaryl-$C_1$-$C_6$- alkyl radical wherein the hetaryl group is selected from the consisting of picolyl, thienyl or furfuryl;
- $R_5$ is a hydrogen atom or a lower alkyl radical; and
- X is an oxygen or sulfur atom or an imino group.

2. Compound of claim 1, wherein at least one of $R_1$ and $R_2$ is methyl, ethyl, n-propyl, isopropyl, butyl, isobutyl, pentyl or isopentyl.

3. Compound of claim 2, wherein at least one of $R_1$ and $R_2$ is methyl.

4. Compound of claim 3, wherein both or $R_1$ and $R_2$ are methyl.

5. Compound of claim 1, wherein at least one of $R_1$ and $R_2$ are allyl, butenyl, isobutenyl, pentenyl or isopentenyl.

6. Compound of claim 5, wherein at least one of $R_1$ and $R_2$ is allyl.

7. Compound of claim 1, wherein $R_1$ and $R_2$, together with the carbon atom to which they are attached, form a cyclopropyl, cyclopentyl or cyclohexyl ring.

8. Compound of claim 1, wherein at least one of $R_3$ and $R_4$ are methyl, propyl, isopropyl, neopentyl or n-hexyl.

9. Compound of claim 1, wherein at least one of $R_3$ and $R_4$ is allyl, or isobutenyl.

10. Compound of claim 1, wherein at least one of $R_3$ and $R_4$ is cyclopropyl, cyclohexyl or cycloheptyl.

11. Compound of claim 10, wherein at least one of $R_3$ and $R_4$ is cyclopropyl or cyclohexyl.

12. Compound of claim 1, wherein at least one of $R_3$ and $R_4$ is cyclopentenyl or cyclohexenyl.

13. Compound of claim 1, wherein at least one of $R_3$ and $R_4$ is a benzyl radical.

14. Compound of claim 1, wherein $R_5$ is methyl, ethyl or propyl.

15. Compound of claim 1, wherein said compound is 4-imino-5- methyleneimidazolidin-2-one.

16. Compound of claim 1, wherein said compound is 4-imino-5- ethylideneimidazolidin-2-one.

17. Compound of claim 1, wherein said compound is 4-imino-5-isopropyideneimidazolidin-2-one.

18. Compound of claim 1, wherein said compound is 3-benzyl-imino-5-methyleneimidazolidin-2-one.

19. Pharmaceutical composition suitable for producing an immunosuppressive effect, said composition comprising an effective amount of a compound of claim 1 and a pharmaceutically acceptable carrier therefor.

20. A method of producing an immunosuppressive effect in a patient in need of said effect, said method comprising administering to said patient an immunosuppressive effective amount of a compound of claim 1.

21. Method of claim 20, wherein said patient requires the suppression of B cell proliferation or B cell activation.

22. Method of claim 21, wherein said amount is from 0.1 to 100 mg per kg of body weight per day.

23. Method of claim 22, wherein said amount is 5 to 50 mg/kg.

24. Method of claim 23, wherein said amount is 5 to 20 mg/kg.

25. Compound of claim 1, wherein both of $R_1$ and $R_2$ are hydrogen.

26. Compound of claim 1, wherein both of and R* are hydrogen.

27. Compound of claim 1, wherein $R_5$ is hydrogen.

28. Compound of claim 1, wherein said compound is 3-methyl-4-imino-5-methyleneimidazolidin-2-one.

29. Compound of claim 1, wherein said compound is 3-n-propyl-4-imino-5-methyleneimidazolidin-2-one.

30. Compound of claim 1, wherein said compound is 3-(2,2-dimethylpropyl)-4-imino-5-methyleneimidazolidin-2-o 31. Compound of claim wherein said compound is 3-(4-pyridylmethyl)-4-imino-5-methyleneimidazolidin-2-one.

32. Compound of claim 1, wherein said compound is 3-phenyl-4-imino-5-methyleneimidazolidin-2-one.

33. Compound of the formula

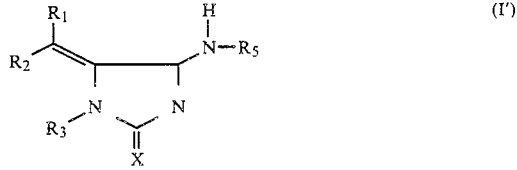

(I')

wherein
- $R_1$ and $R_2$ which can be the same or different, are a hydrogen atom, a $C_1$-$C_5$ alkyl radical, a $C_3$-$C_5$ alkenyl radical, a phenyl are attached, form a saturated or unsaturated hydrocarbon $C_3$-$C_7$ ring;
- $R_3$ is a hydrogen atom, a straight chained or branched $C_1$-$C_{10}$ alkyl radical, a straight-chained or branched $C_3$-$C_7$; alkenyl radical, a $C_3$-$C_7$ cycloalkyl radical, a $C_3$-$C_7$ cycloalkenyl radical, phenyl radical, a $C_6$-$C_{10}$-aryl-$C_1$-$C_6$-alkyl radical, or a hetaryl-$C_1$-$C_6$-alkyl radical wherein the hetaryl group is selected from the consisting of picolyl, thienyl or furfuryl;
- $R_5$ is a hydrogen atom or a lower alkyl radical; and
- X is an oxygen or sulfur atom or an imino group.

* * * * *